(12) United States Patent
Bak

(10) Patent No.: US 7,600,434 B2
(45) Date of Patent: Oct. 13, 2009

(54) MECHANISM FOR REMOTELY MEASURING MEDICAL TREATMENT SYSTEM BED DEFLECTION

(75) Inventor: Donald J. Bak, Streamwood, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 103 days.

(21) Appl. No.: 11/948,307

(22) Filed: Nov. 30, 2007

(65) Prior Publication Data

US 2009/0139032 A1 Jun. 4, 2009

(51) Int. Cl.
*G01N 3/20* (2006.01)
(52) U.S. Cl. ...................................... 73/849
(58) Field of Classification Search ............ 73/760–854
See application file for complete search history.

(56) References Cited

U.S. PATENT DOCUMENTS

| | | | |
|---|---|---|---|
| 4,793,428 A * | 12/1988 | Swersey | 177/144 |
| 4,953,244 A * | 9/1990 | Koerber et al. | 5/600 |
| 5,393,938 A * | 2/1995 | Bumbalough | 177/144 |
| 5,672,849 A * | 9/1997 | Foster et al. | 177/144 |

* cited by examiner

*Primary Examiner*—Max Noori

(57) ABSTRACT

A bed for a medical treatment system. The system has a medical treatment device, such as a CT scanner or radiation therapy system, oriented in a spatial relationship with the bed. The bed has an elevation member, a support member for a patient subject, one section of the support member being mounted on the elevation member and the remaining section of the support member being cantilevered from the elevation member, a mount arranged to the support member, an attachment member arranged at the remaining section of the support member, a deflection member connecting the mount and the attachment member, and a sensor arranged on the deflection member. The sensor is in communication with a deflection calculation apparatus that correlates deflection measured by the sensor with the spatial relationship between the bed and the medical treatment device.

20 Claims, 3 Drawing Sheets

| 310 | Sensing with the sensor(s) the deflection of the deflection member |

| 320 | Calculating deflection of support member based on the sensed deflection of the deflection member(s) |

*Figure 4*

MECHANISM FOR REMOTELY MEASURING MEDICAL TREATMENT SYSTEM BED DEFLECTION

TECHNICAL FIELD

The technical field of the present invention relates to a patient support device having a cantilevered support member for a patient and to a mechanism for remotely measuring bed deflection. More particularly, the hereinafter described device and method allows the deflection of the cantilevered support member to be assessed.

BACKGROUND

It is frequently necessary to position a patient in relation to medical devices. For example, in medical imaging methods, such as X-ray, a patient located on a recumbent board (cantilevered support means or member) is frequency displaced relative to a scan region of a diagnostic apparatus during examination. In many cases, the recumbent board is supported only at one end to allow access to a patient lying on the board. Therefore, it inevitably bends with increasing forward displacement of the recumbent board or with a heavy patient resting on the recumbent board. The deflection cannot be completely avoided even with a recumbent board that is designed to minimize instability.

For large patients the current designs of beds are extremely rigid and subsequently large. Additional support at the rear end of a cantilevered support member for a patient is required to counter act further deflection of the cantilever. This limits the deflection at the worst case situation to a known minimum that is an acceptable value. The position of the bed can be compensated if the deflection is known. The deflection could be measured by using strain sensors attached to the bed. However, the material of the sensors and wires would cause artifacts in the calculation of deflection. Determining the compensation by estimating the deflection based on the weight of a patient is insufficient because the distribution of the weight of the patient is not uniform.

In a more specific example of background art, such as radiation therapy systems, the patient is placed horizontally on a patient tabletop, and then positioned laterally and vertically such that a diseased region to be irradiated comes to be located precisely in the iso-center (the intersection of the horizontal and vertical axes at the treatment center). To enable performing this positioning exactly, the patient is as a rule marked beforehand in a simulator, and/or the tumor is located exactly beforehand using an imaging device. To achieve adequate positioning of the diseased tissue in the iso-center, the 3-D data obtained for instance in a computed tomography are also transmitted to the radiation therapy system, where they are used for patient positioning, or else the patient is oriented on the therapy system by means of markings made on the patient—for instance, using what is known as a "laser cross" (i.e., a projected cross-hair or target). The patient tabletop is supported by a lifting column disposed eccentrically to the iso-center. For reasons of structural height, among others, a load-bearing element that supports the patient tabletop and is supported rotatably about the vertical iso-axis is as a rule mounted at least in part in a well or a tub in the floor. Radiation therapy systems or patient support devices of the above type have been described for instance in U.S. Pat. No. 4,885,998. The problem in these systems is that the relative positioning of the patient and the medical device is made inaccurate by the deflection caused by the weight of the patient on the patient tabletop.

Additionally, a deflection of a bed is not uniform, because the weight distribution of a patient is not uniform. For example, the area of the bed supporting the head of a patient would deflect less compared with the area of the bed supporting the torso of a patient. Consequently, the deflection of the bed is not accurately assessed when only considering a point on the cantilevered bed.

In view of the prior art discussed above, there is a need to provide a device and method allowing for a more precise calculation and assessment of the deflection of a support member for patients than the conventional prior art. This would allow a more accurate positioning of patients on the support member in relation to medical devices. Further, good spatial information of the relevant part of the patient can be assessed. Hereby patients can be treated in a more target-specific manner resulting in, for example, reduced radiation dosage when X-rayed.

There also exists a need to minimize the structure of the support member and avoid a rear end support for the cantilever. The construction of the support member should be simple from a technical and an economical perspective.

Additionally, it is desirable to avoid cumbersome arrangements that would interfere with the field of view around the support member of the patient.

SUMMARY

According to an embodiment, a bed may comprise an elevation member, a support member for a subject, one section of the support member being mounted on the elevation member and the remaining section of the support member being cantilevered from the elevation member, a mount arranged to the support member, an attachment member arranged at the remaining section of the support member, a deflection member connecting the mount and the attachment member, and a sensor arranged on the deflection member.

In a further embodiment, the deflection member is located remotely from the support member by the mount and the attachment member. Preferably, the deflection member comprises the same material as the support member.

In a further embodiment, the mount is arranged to the one section of the support member being mounted on the elevation member.

According to further embodiments, additional sets of the mount, the attachment member, and the deflection member are arranged at different locations on the support member. In one embodiment the attachment member of the additional sets may be arranged at different locations along the width of the remaining section of the support member. In one embodiment a sufficient number of additional sets may be arranged to provide an estimate of the deflection of locations along the cantilevered support member to determine a necessary compensation for achieving a required accuracy of the relative position of the support member of the bed.

In further embodiments, the sensor may be one or more sensor(s) selected from the group consisting of: strain gauge, piezoresistor, resistor gauge, semiconductor gauge, foil gauge, mechanical gauge, mercury strain gauge, force transducer, load cell or similar.

In one embodiment, a method for assessing bed deflection for a bed according to the embodiments described above may comprise the steps of sensing with the sensor the deflection of the deflection member, and calculating the deflection of the support member based on the deflection of the deflection member. In one embodiment, the sensed deflection is a deflection remote from the support member.

In a further embodiment, additional sets of the mount, the attachment member, and the deflection member are arranged at different locations on the support member for calculating the deflection.

In a further embodiment, the attachment member of the additional sets is arranged at different locations along the width of the remaining section of the support member.

In a further embodiment, a sufficient number of additional sets are arranged to provide an estimate of the deflection of locations along the cantilevered support member to determine a necessary compensation for achieving a required accuracy of the relative position of the support member of the bed.

In one embodiment, a bed may comprise an elevation member, a support member for a subject, one section of the support member being mounted on the elevation member and the remaining section of the support member being cantilevered from the elevation member, and at least one set comprising a mount arranged to the support member, an attachment member arranged at the remaining section of the support member, a deflection member connecting the mount and the attachment member and located remotely from the support member by the mount and the attachment member, and a sensor arranged on the deflection member.

In a further embodiment, the mount may be arranged to the one section of the support member being mounted on the elevation member.

In embodiments, additional sets of the mount, the attachment member, and the deflection member may be arranged at different locations on the support member. In one embodiment, the attachment member of the additional sets may be arranged at different locations along the width of the remaining section of the support member. In one embodiment, a sufficient number of additional sets may be arranged to provide an estimate of the deflection of locations along the cantilevered support member to determine a necessary compensation for achieving a required accuracy of the relative position of the support member of the bed.

In an embodiment, the deflection member may comprise the same material as the support member.

In embodiment, the sensor may be one or more sensor(s) selected from the group consisting of: strain gauge, piezoresistor, resistor gauge, semiconductor gauge, foil gauge, mechanical gauge, mercury strain gauge, force transducer, load cell or similar.

Other technical advantages of the present disclosure will be readily apparent to one skilled in the art from the following description and claims. Various embodiments of the present application obtain only a subset of the advantages set forth. No one advantage is critical to the embodiments. Any claimed embodiment may be technically combined with any preceding claimed embodiment(s).

BRIEF DESCRIPTION OF THE DRAWINGS

The accompanying drawings, which are incorporated in and constitute a part of the specification, illustrate presently preferred embodiments, and together with the general description given above and the detailed description of the exemplary embodiments given below, serve to explain, by way of example, the principles of the invention.

FIG. 4 shows a flow chart of a method for assessing bed deflection for a bed according to an embodiment.

DETAILED DESCRIPTION

The hereinafter described embodiments may provide a device and method allowing for a more precise calculation and assessment of the deflection of a support member for patients than the conventional devices. This would allow a more accurate positioning of patients on the support member in relation to medical devices. Further, good spatial information of the relevant part of the patient can be assessed. Hereby, patients can be treated in a more target-specific manner resulting in, for example, reduced radiation dosage when X-rayed.

The hereinafter described embodiments may further provide a device and method minimizing the structure of the support member and avoiding a rear end support for the cantilever. The construction of the support member may be simple from a technical perspective and may be more economic.

Additionally, cumbersome arrangements that would interfere with the field of view around the support member of the patient are avoided.

Figure 1:
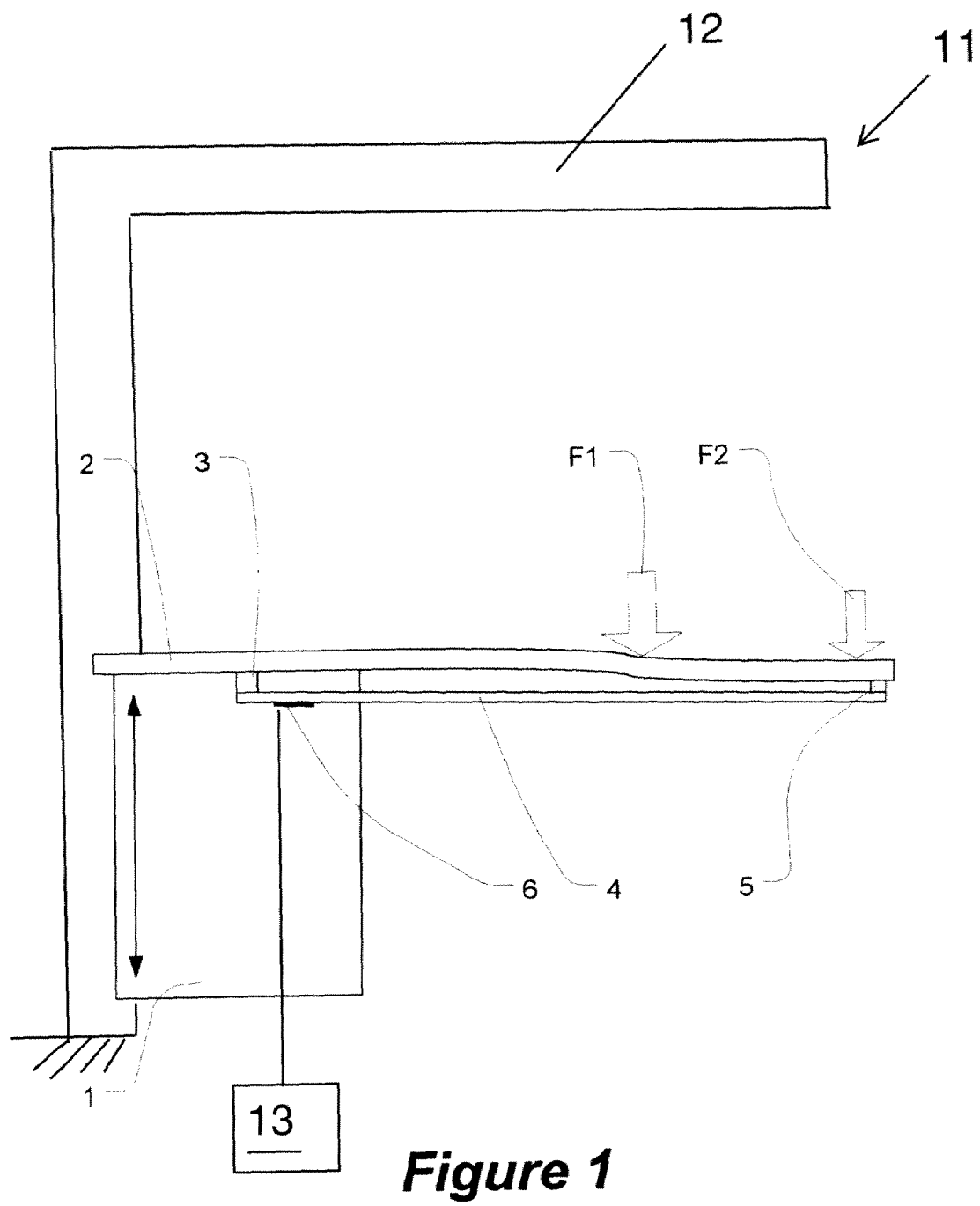
FIG. 1 shows a mechanism for remotely measuring bed deflection according to one embodiment.

A problem is, that the deflection of a bed is not uniform, because a subject's weight distribution symbolized by arrows F1 and F2 in FIG. 1 is not uniform. Consequently, the deflection of the bed can not be accurately assessed by only considering a point on the bed or the weight of the patient.

FIG. 1 shows an embodiment wherein a bed is provided for a subject, such as for example a patient. This kind of bed may, according to an embodiment, be used in a medical treatment system 11, where a patient may be positioned relative to a medical treatment device 12. The bed comprises an elevation member 1 and a support member 2 for the subject. The support member 2 is mounted on the elevation member 1. As indicated by the vertical arrow, elevation member 1 allows for vertical displacement of the support member 2 and, thus, comprises a respective elevation lift or displacement mechanism.

According to an embodiment, one section of the support member 2 is mounted on the elevation member 1 and the remaining section of the support member 2 is consequently cantilevered from the elevation member 1.

It is this remaining section that deflects when a subject is positioned on top of the support member 2. Since the weight distribution of a subject is not uniform, the deflection of the support member 2 is not uniform. Consequently, the deflection of the support member can not be accurately assessed when only a point of the cantilevered bed is considered. The force caused by the weight of the subject on the support member 2 has been indicated with the two arrows marked F1 and F2 in FIG. 1.

A mount 3 is arranged to the support member 2. The mount 3 may be arranged on any location on the support member. According to one embodiment, a location to arrange the mount 3 may be the section of the support member 2 mounted to the elevation member 1. In this way the mount 3 would be hidden by the elevation member 1 and the support member 2 and would not be visible at the support member 2 of the bed. This would have the advantage that the mount 3 is not interfering with any medical device 12 used in connection with the bed.

According to one embodiment, an attachment member 5 is arranged at the remaining section of the support member 2. According to one embodiment, a location to arrange the attachment member 5 is at the end of the cantilevered support member 2. However, according to other embodiments, any location at the remaining section of the support member that is cantilevered may be used for this purpose. In fact, several locations stretching over the entire length and entire width of the cantilevered support member 2 can be used according to various embodiments, because this gives several additional possibilities for assessing the deflection of the support member 2.

Deflection coupling means such as a deflection member 4 connects the mount 3 and the attachment member 5. The deflection member 4 can be in any suitable form, such as for example a rod, bar, elongate member, or beam. The technical function of the deflection member 4 may be to transfer uniformly and remotely from the support member 2 the deflection of the support member 2. According to an embodiment, one end of the deflection member 4 can be attached to the mount 3 and the other end can be attached to the attachment member 5. A relative displacement between the mount 3 and the attachment member 5 is caused by the weight of a subject on the support member 2. The relative displacement between the mount 3 and the attachment member 5 causes the deflection member 4 to deflect. This deflection is transmitted uniformly through out the deflection member 4. The deflection of the deflection member 4 is different from the deflection of the support member 2 caused by the subject. This is because the deflection of the support member is not uniform since the weight distribution of a subject is not uniform. For example, the weight corresponding to F1 of a part of a subject, for example the stomach of a patient, causes the support member 2 to deflect differently at one specific location than at another specific location of the support member 2, caused by the weight corresponding to F2 of another part of a subject, for example the head of a patient. By transferring the relative displacement between the mount 3 and the attachment member 5 to a remotely arranged deflection member 4, a uniform deflection is achieved in the deflection member 4. Hereby the relative displacement between the mount 3 and the attachment member 5 can be assessed accurately.

A sensor 6 is arranged on the deflection member 4 and is coupled to a deflection calculation apparatus 13. According to an embodiment, the sensor 6 may be arranged on the deflection member 4 at a location or section close to the mount 3. In this way the sensor 6 would be hidden by the elevation member 1 and the support member 2 and would not be visible at the support member 2 of the bed. This would have the advantage of the sensor 6 not interfering with any medical device 12 used in connection with the bed. However, the sensor 6 may also be arranged at any location or section of the deflection member 4.

Any kind of sensor may be used. According to an embodiment, a sensor is a strain gauge. However, the sensor may also be a resistor gauge, semiconductor gauge, foil gauge, mechanical gauge, and/or mercury strain gauge. Further possible sensors are piezoresistors, force transducers, load cells and/or similar. A combination of the sensors mentioned is also possible.

According to one embodiment the deflection member 4 is located remotely from the support member 2 by the mount 3 and the attachment member 5. Hereby the deflection of the support member 2 does not interfere with the deflection of the deflection member 4 and the deflection member 4 can maintain a uniform deflection. According to an embodiment, the deflection member 4 may comprise the same material as the support member. The deflection member 4 may be of any suitable form, such as for example a rod, bar, elongate member, or beam. The cross section of the deflection member 4 may be in any suitable shape that transforms deflection uniformly, such as for example I-shaped, U-shaped, X-shaped, rectangular, or any form of circular shape. The deflection member 4 could be made solely from the same material as the support member 2 or contain other material additionally. This would allow the deflection member 4 to deflect and react to the environment in a similar way as the support member 2. However, the deflection member 4 could be made from a material different from that of the support member 2.

Figure 2:
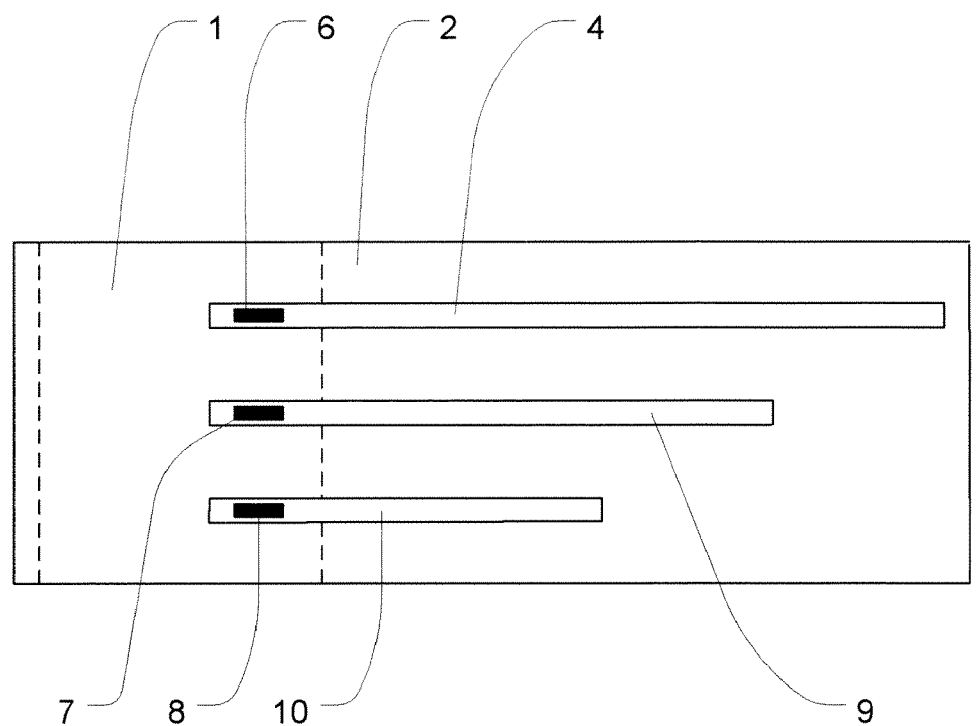
FIG. 2 shows, in a view of the underside of a bed, a mechanism for remotely measuring bed deflection with additional sets of deflection members according to an embodiment.

FIG. 2 shows an embodiment of a mechanism for remotely measuring bed deflection with additional sets of deflection members. The view of FIG. 2 is of the underside of the support member 2. The position of the elevation member 1 has been indicated by dashed lines. By way of example three sets of the deflection member 4 are shown in FIG. 2. A shorter deflection member 10 with a sensor 8 arranged at the deflection member 10, a long deflection member 4 with a sensor 6 arranged at the deflection member 4, and a deflection member 9 of an intermediate length with a sensor 7 arranged to the deflection member 9. However, any number of sets may be used.

In one embodiment the bed comprises additional sets of the mount 3, the attachment member 5, and the deflection member 4. These additional sets are arranged at different locations at the support member 2. According to an embodiment, the attachment member of the additional sets can be arranged at different locations along the width of the remaining section of the support member. In a further embodiment, a sufficient number of additional sets are arranged to provide an estimate of the deflection of locations along the cantilevered support member 2 to determine a necessary compensation for achieving a required accuracy of the relative position of the support member 2 of the bed. The sufficient number of additional sets depends on the required accuracy desired. A higher number of additional sets allows for a higher degree of accuracy.

The arrangement of additional sets of the mount 3, the attachment member 5, and the deflection member 4 allows for assessing or monitoring additional locations along the deflected support member 2. For each additional set the deflection of at least one location on the support member 2 can be assessed. By selecting a number of locations to be assessed or monitored, an estimate of the deflection along the cantilevered support member 2 can be made. The amount the support member 2 is deflecting can be calculated by the deflection calculation apparatus 13 by using the estimates. Using the calculated deflection amounts in a reconstruction algorithm employed by the medical treatment system 11, the support member 2 actual deflection can be compensated. For example, a simple reconstruction algorithm could be based on a simple linear sectional approach. By the compensation, the support member 2 is positioned accurately in space, or more specifically, in relation to a medical device 12. This physical compensation can, for example, be done by the elevation member 1.

As will be appreciated by this description, an embodiment of the bed may include an elevation member 1, a support member 2 for a subject, one section of the support member 2 being mounted on the elevation member 1 and the remaining section of the support member 2 being cantilevered from the elevation member, and at least one set. The set comprising a mount 3 arranged to the support member 2, an attachment member 5 arranged at the remaining section of the support member 2, a deflection member 4 connecting the mount and the attachment member 5 and located remotely from the support member 2 by the mount 3 and the attachment member 5, and a sensor 6 arranged on the deflection member 4. This combination of described features will allow for a high degree of deflection assessment. These additional sets are arranged at different locations at the support member 2. According to an embodiment, the attachment member 5 of the additional sets can be arranged at different locations along the width of the remaining section of the support member 2. In a further embodiment, a sufficient number of additional sets are arranged to provide an estimate of the deflection of locations along the cantilevered support member 2 to determine a necessary compensation for achieving a required accuracy of the relative position of the support member 2 of the bed. The sufficient number of additional sets depends on the required accuracy desired. A high number of additional sets allows for a high degree of accuracy.

Figure 3:
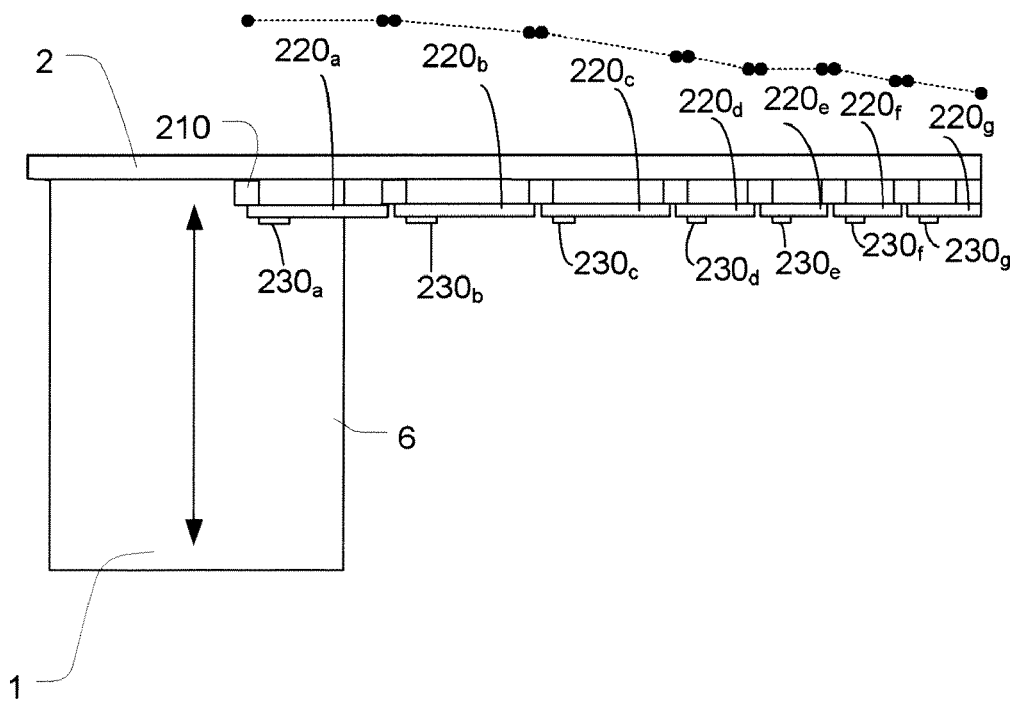
FIG. 3 shows another embodiment of a mechanism for remotely measuring bed deflection.

FIG. 3 shows yet another embodiment in which a plurality of mounts 210 are arranged along the length of the support member 2. Between each section defined by two adjacent mounts 210, a deflection member 220*a* . . . 220*g* is arranged. Each deflection member 220*a* . . . 220*g* comprises an associated sensor 230*a* . . . 230*g*. This arrangement allows for a more precise approximation of an actual deflection of the support member 2. Such a linear approximation is shown by the dotted line above each reference sign 220*a* . . . 220*g*. Each segment represents one linear approximation for an associated segment. By providing measurement signals from each sensor 230*a* . . . 230*g* a processor can calculate such a linear approximation. In case the support member comprises an area in which a higher resolution is desirable, the distance of each segment can be shortened. The embodiment shown in FIG. 3, for example, assumes that a higher resolution is desirable the farther the support member extends from the elevation member 1. Thus, the respective distances between the mounts 210 along the length of support member 2 are shortened the farther they are located from elevation member 1. However, if other areas of support member 1 are of particular interest the resolution of the linear approximation by using multiple deflection members can be respectively adapted. The embodiment shown in FIG. 3 can also be combined with the embodiment shown in FIG. 2.

FIG. 4 shows a flow chart of a method for assessing bed deflection by the deflection calculation apparatus 13 for a bed according to an embodiment. The method for assessing bed deflection may comprise the following steps in any order. As shown by example in FIG. 3, a first step 310 may be sensing with the sensor 6 or the sensors 6, 7, 8; or 230*a* . . . 230*g* the deflection of the deflection member 4 or members 4, 9, 10 or members 220*a* . . . 220*g*, followed by a second step of calculating the deflection of the support member 2 based on the deflection of the respective deflection member(s) 4, 9, 10; 220*a* . . . 220*g*. Furthermore, in one embodiment, when calculating the deflection in step 320, additional sets of the mount 3, the attachment member 5, or mounts 210 and the deflection member 4, 9, 10; 220*a* . . . 220*g* are arranged at different locations at the support member 2. According to an embodiment, the attachment member 5, or members 210 of the additional sets can, thus, be arranged at different locations along the width and/or length of the remaining section of the support member. Several locations stretching over the entire length and entire width of the cantilevered support member 2 may, thus, be used according to an embodiment, because this provides for several additional possibilities and/or higher accuracy for assessing the deflection of the support member 2.

In one embodiment a sufficient number of additional sets can be arranged to provide an estimate or approximation of the deflection of locations along the cantilevered support member 2. As explained above, hereby the necessary compensation for achieving a required accuracy of the relative position of the support member 2 of the bed can be determined.

In one embodiment a field of view is defined as the area surrounding the remaining section of the support member and a portion of the deflection member is mounted in the field of view. According to an embodiment, the mount can be arranged to the support member outside the field of view. Similarly, the sensor could be arranged on the deflection member outside the field of view. In this way the mount and the sensor would not affect the field of view of the cantilevered support member.

The device and method discussed above assesses the deflection of support member for a patient. The invention, therefore, is well adapted to carry out the objects and attain the ends and advantages mentioned, as well as others inherent therein. While the invention has been described and is defined by reference to particular preferred embodiments of the invention, such references do not imply a limitation on the invention, and no such limitation is to be inferred. The invention is capable of considerable modification, alteration, and equivalents in form and function, as will occur to those ordinarily skilled in the pertinent arts. The described preferred embodiments of the invention are exemplary only, and are not exhaustive of the scope of the invention. Consequently, the invention is intended to be limited only by the spirit and scope of the appended claims, giving full cognizance to equivalents in all respects.

What is claimed is:

1. A medical treatment system comprising:
a medical treatment device;
a bed oriented spatially relative to the medical treatment device, the bed having:
an elevation member;
a support member for a subject, one section of the support member being mounted on the elevation member and the remaining section of the support member being cantilevered from the elevation member;
a mount arranged on the support member;
an attachment member arranged at the remaining section of the support member; and
a deflection member connecting the mount and the attachment member;
a sensor arranged on the deflection member for measuring deflection member deflection; and
a deflection calculation apparatus in communication with the sensor, for correlating measured deflection with the spatial orientation between the bed and the medical treatment device.

2. The system according to claim 1, wherein the deflection member is located remotely from the support member by the mount and the attachment member.

3. The system according to claim 2, wherein the mount is arranged to the one section of the support member being mounted on the elevation member.

4. The system according to claim 1, wherein additional sets of the mount, the attachment member, and the deflection member are arranged at different locations on the support member.

5. The system according to claim 4, wherein the attachment members of the additional sets are arranged at different locations along at least one of the width or length of the remaining section of the support member.

6. The system according to claim 5, wherein a number of additional sets are arranged to provide an estimate of the deflection of locations along the cantilevered support member to determine a necessary compensation for achieving a required accuracy of the relative position of the support member of the bed and the medical treatment device.

7. The system according to claim 1, wherein the deflection member comprises the same material as the support member.

8. The system according to claim 1, wherein the sensor is one or more sensors selected from the group consisting of: strain gauge, piezoresistor, resistor gauge, semiconductor gauge, foil gauge, mechanical gauge, mercury strain gauge, force transducer, or load cell.

9. In a medical treatment system having a medical treatment device; a bed oriented spatially relative to the medical treatment device, the bed having: an elevation member, a support member for a subject, one section of the support member being mounted on the elevation member and the remaining section of the support member being cantilevered from the elevation member, a mount arranged on the support member, an attachment member arranged at the remaining section of the support member, and a deflection member connecting the mount and the attachment member; a sensor arranged on the deflection member; and a deflection calculation apparatus in communication with the sensor; a method for correlating bed deflection with spatial orientation between the bed and the medical treatment device comprising the steps of:

sensing with the sensor deflection of the deflection member; and calculating with the deflection calculation apparatus the deflection of the support member based on the sensed deflection of the deflection member; and correlating spatial orientation between the bed and the medical treatment device with the calculated deflection.

10. The method according to claim 9, wherein the sensed deflection is a deflection remote from the support member.

11. The method according to claim 9, wherein additional sets of the mount, the attachment member, and the deflection member are arranged at different locations on the support member, for calculating the deflection.

12. The method according to claim 11, wherein the attachment members of the additional sets are arranged at different locations along at least one of the width or length of the remaining section of the support member.

13. The method according to claim 11, wherein a number of additional sets are arranged to provide an estimate of the deflection of locations along the cantilevered support member to determine a necessary compensation for achieving a required accuracy of the relative position of the support member of the bed and the medical treatment device.

14. A medical treatment system comprising:
a medical treatment device;
a bed oriented spatially relative to the medical treatment device, the bed having:
an elevation member,
a support member for a subject, one section of the support member being mounted on the elevation member and the remaining section of the support member being cantilevered from the elevation member, and
at least one set having:
a mount arranged on the support member,
an attachment member arranged at the remaining section of the support member, and
a deflection member connecting the mount and the attachment member;
a sensor arranged on the deflection member for measuring deflection member deflection; and
a deflection calculation apparatus in communication with the sensor, for correlating measured deflection with the spatial orientation between the bed and the medical treatment device.

15. The system according to claim 14, wherein the first section of the support member is located adjacent to the elevation member.

16. The system according to claim 14, wherein additional sets of the mount, the attachment member, and the deflection member are arranged at different locations on the support member.

17. The system according to claim 16, wherein the attachment members of the additional sets are arranged at different locations along at least one of the width or length of the remaining section of the support member.

18. The bed according to claim 14, wherein a number of additional sets are arranged to provide an estimate of the deflection of locations along the cantilevered support member to determine a necessary compensation for achieving a required accuracy of the relative position of the support member of the bed and the medical treatment device.

19. The system according to claim 14, wherein the deflection member comprises the same material as the support member.

20. The system according to claim 14, wherein the sensor is one or more sensors selected from the group consisting of: strain gauge, piezoresistor, resistor gauge, semiconductor gauge, foil gauge, mechanical gauge, mercury strain gauge, force transducer, or load cell.

* * * * *